(12) United States Patent
Park et al.

(10) Patent No.: US 11,384,120 B2
(45) Date of Patent: Jul. 12, 2022

(54) PEPTIDE CAPABLE OF BINDING TO BIOMARKER FOR INFLAMMATORY AND METABOLIC DISEASES, AND USE THEREOF

(71) Applicant: NIBEC CO., LTD., Chungcheongbuk-do (KR)

(72) Inventors: Yoon Jeong Park, Seoul (KR); Chong-Pyoung Chung, Seoul (KR); Jue-Yeon Lee, Gyeonggi-do (KR)

(73) Assignee: NIBEC CO., LTD., Chungcheongbuk-do (KR)

( * ) Notice: Subject to any disclaimer, the term of this patent is extended or adjusted under 35 U.S.C. 154(b) by 0 days.

(21) Appl. No.: 17/271,739

(22) PCT Filed: Aug. 29, 2019

(86) PCT No.: PCT/KR2019/011036
§ 371 (c)(1),
(2) Date: Feb. 26, 2021

(87) PCT Pub. No.: WO2020/046001
PCT Pub. Date: Mar. 5, 2020

(65) Prior Publication Data
US 2021/0355164 A1 Nov. 18, 2021

(30) Foreign Application Priority Data
Aug. 28, 2019 (KR) .......................... 10-2019-0105916

(51) Int. Cl.
*C07K 7/08* (2006.01)
*A61K 38/00* (2006.01)
*A61P 1/16* (2006.01)
*A61P 1/00* (2006.01)

(52) U.S. Cl.
CPC .................. *C07K 7/08* (2013.01); *A61P 1/00* (2018.01); *A61P 1/16* (2018.01); *A61K 38/00* (2013.01); *C07K 2319/10* (2013.01)

(58) Field of Classification Search
None
See application file for complete search history.

(56) References Cited

U.S. PATENT DOCUMENTS 5,595,756 A * 1/1997 Bally .................... A61K 9/1272
264/4.1

FOREIGN PATENT DOCUMENTS

| KR | 20110137236 A | 12/2011 |
| KR | 101356811 B1 | 2/2014 |
| KR | 101652957 B1 | 9/2016 |
| WO | 2017030966 A1 | 2/2017 |

OTHER PUBLICATIONS

Bergantin LB. Diabetes and inflammatory diseases: An overview from the perspective of Ca2+/3'-5'-cyclic adenosine monophosphate signaling. World J Diabetes. Jun. 15, 2021;12(6):767-779 (Year: 2021).*
Sporn et at, "Chemoprevention of Cancer," Carcinogenesis, vol. 21 (2000), 525-530 (Year: 2000).*
Zugazagoitia et al, Current Challenges in Cancer Treatment, Clinical Therapies, vol. 38, (2016), pp. 1551-1566 (Year: 2016).*
Zhao, J. et al., "The common stress responsive transcription factor ATF3 binds genomic sites enriched with p300 and H3K27ac for transcriptional regulation", BMC Genomics, 17(335), DOI 10.1186/s12864-016-2664-8, 2016, 1-14.
Fan, G. et al., "Sequence-dependent peptide surface functionalization of metal-organic frameworks", ACS applied Materials & Interfaces, vol. 10(22) (online at https://pubs.acs.org/doi/abs/10.1021/acsami.8b05148), May 15, 2018, 18601-18609.
Jadhav, K. et al., "Activating transcription factor 3 in immune response and metabolic regulation", Liver Research, vol. 1, 2017, 96-102.
Jang, M. et al., "ATF3 plays a role in adipocyte hypoxia-mediated mitochondria dysfunction in obesity," Biochem. Biophys. Res. Commun., vol. 431, No. 3: 421-427 (2013).
Kalfon, R. et al., "ATF3 expression in cardiomyocytes preserves homeostasis in the heart and controls peripheral glucose tolerance", Cardiovascular Res., vol. 113, 2017, 134-146.
Lai, P. et al., "ATF3 Protects against LPS-Induced Inflammation in Mice via Inhibiting HMGB1 Expression," Evidence-Based Complementary and Alternative Medicine, 2013: 1-14, Article ID 716481, 2013.

(Continued)

*Primary Examiner* — Thomas S Heard
(74) *Attorney, Agent, or Firm* — Elmore Patent Law Group, P.C.; Joseph C. Zucchero; Carolyn S. Elmore (57) ABSTRACT

The present invention pertains to: a peptide having ATF3-binding ability and represented by any one amino acid sequence selected from the group consisting of SEQ ID NOs: 1 to 4; a fused peptide in which a cell-permeable peptide is bound to the peptide having ATF3-binding ability; and a use of the peptides for the treatment of inflammatory diseases, metabolic diseases, autoimmune diseases and/or fibrotic diseases. According to the present invention, a novel peptide having the ability to bind to ATF3, which is a protein serving as a biomarker and an important factor in the occurrence of various inflammatory diseases, metabolic diseases, autoimmune diseases and/or fibrotic diseases, is provided to thereby regulate the intracellular concentration of ATF3, and can thus be used for the treatment of inflammatory diseases, metabolic diseases, autoimmune diseases and/or fibrotic diseases. Moreover, the disease treatment effect can be enhanced by further fusing a peptide having intracellular permeability and an inflammation inhibitory function to the peptide.

8 Claims, 4 Drawing Sheets
Specification includes a Sequence Listing.

(56) References Cited

OTHER PUBLICATIONS

Lee, J. Y. et al., "Identification of a cell-penetrating peptide domain from human betadefensin 3 and characterization of its anti-inflammatory activity", Int J Nanomedicine, vol. 10 (online at 1 DOI: 10.2147/IJN.S90014), Aug. 26, 2015, 5423-2534.

Smith, C., et al., "Lupus high-density lipoprotein induces proinflammatory responses in macrophages by binding lectin-like oxidised low-density lipoprotein receptor 1 and failing to promote activating transcription factor 3 activity," Ann. Rheum. Dis., Published Online First: Aug. 19, 2016. doi: 10.1136/annrheumdis-2016-209683.

Zheng, S. et al., "NF-κB1 Inhibits NOD2-Induced Cytokine Secretion through ATF3-Dependent Mechanisms," Mol. Cell. Biol., vol. 33(24): 4857-4871 (2013).

Zhou, H. et al., "Activating transcription factor 3 in cardiovascular diseases: a potential therapeutic target," Basic Res. Cardiol., vol. 113, No. 37, Published online Aug. 9, 2018.

\* cited by examiner

SEQUENCE LISTING

```
<160> NUMBER OF SEQ ID NOS: 33

<210> SEQ ID NO 1
<211> LENGTH: 12
<212> TYPE: PRT
<213> ORGANISM: Artificial Sequence
<220> FEATURE:
<223> OTHER INFORMATION: ATF3 binding peptide

<400> SEQUENCE: 1

Ala Glu Ser Pro Leu Thr Asn Arg Gly Trp Asn Pro
1               5                   10

<210> SEQ ID NO 2
<211> LENGTH: 12
<212> TYPE: PRT
<213> ORGANISM: Artificial Sequence
<220> FEATURE:
<223> OTHER INFORMATION: ATF3 binding peptide

<400> SEQUENCE: 2

Met Leu Asp Thr Asn Ile Gln Ser Arg Pro Asn Leu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: ATF3 binding peptide

<400> SEQUENCE: 3

Thr Leu Gly Leu Arg Pro Val Pro Val Ala Thr Thr
1               5                   10

<210> SEQ ID NO 4
<211> LENGTH: 12
<212> TYPE: PRT
<213> ORGANISM: Artificial Sequence
```

<220> FEATURE:
<223> OTHER INFORMATION: ATF3 binding peptide

<400> SEQUENCE: 4

Val Leu Asn Ile Pro Glu His Phe Thr Ala Gln Asn
1               5                   10

<210> SEQ ID NO 5
<211> LENGTH: 15
<212> TYPE: PRT
<213> ORGANISM: Artificial Sequence
<220> FEATURE:
<223> OTHER INFORMATION: Cell Penetratrating Peptide(hBD-3-3)

<400> SEQUENCE: 5

Gly Lys Cys Ser Thr Arg Gly Arg Lys Cys Cys Arg Arg Lys Lys
1               5                   10                  15

<210> SEQ ID NO 6
<211> LENGTH: 27
<212> TYPE: PRT
<213> ORGANISM: Artificial Sequence
<220> FEATURE:
<223> OTHER INFORMATION: Fusion Peptide of ATF3 binding peptide and Cell
      Penetratrating Peptide

<400> SEQUENCE: 6

Ala Glu Ser Pro Leu Thr Asn Arg Gly Trp Asn Pro Gly Lys Cys Ser
1               5                   10                  15

Thr Arg Gly Arg Lys Cys Cys Arg Arg Lys Lys
            20                  25

<210> SEQ ID NO 7
<211> LENGTH: 27
<212> TYPE: PRT
<213> ORGANISM: Artificial Sequence
<220> FEATURE:
<223> OTHER INFORMATION: Fusion Peptide of ATF3 binding peptide and Cell
      Penetratrating Peptide

<400> SEQUENCE: 7

Met Leu Asp Thr Asn Ile Gln Ser Arg Pro Asn Leu Gly Lys Cys Ser
1               5                   10                  15

Thr Arg Gly Arg Lys Cys Cys Arg Arg Lys Lys
            20                  25

<210> SEQ ID NO 8
<211> LENGTH: 27
<212> TYPE: PRT
<213> ORGANISM: Artificial Sequence
<220> FEATURE:
<223> OTHER INFORMATION: Fusion Peptide of ATF3 binding peptide and Cell
      Penetratrating Peptide

<400> SEQUENCE: 8

Thr Leu Gly Leu Arg Pro Val Pro Val Ala Thr Thr Gly Lys Cys Ser
1               5                   10                  15

Thr Arg Gly Arg Lys Cys Cys Arg Arg Lys Lys
            20                  25

<210> SEQ ID NO 9
<211> LENGTH: 27
<212> TYPE: PRT
<213> ORGANISM: Artificial Sequence
<220> FEATURE:
<223> OTHER INFORMATION: Fusion Peptide of ATF3 binding peptide and Cell Penetratrating Peptide

<400> SEQUENCE: 9

Val Leu Asn Ile Pro Glu His Phe Thr Ala Gln Asn Gly Lys Cys Ser
1               5                   10                  15

Thr Arg Gly Arg Lys Cys Cys Arg Arg Lys Lys
            20                  25

<210> SEQ ID NO 10
<211> LENGTH: 14
<212> TYPE: PRT
<213> ORGANISM: Artificial Sequence
<220> FEATURE:
<223> OTHER INFORMATION: Cell Penetratrating Peptide(LMWP)

<400> SEQUENCE: 10

Val Ser Arg Arg Arg Arg Arg Gly Gly Arg Arg Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Cell Penetratrating Peptide(H4)

<400> SEQUENCE: 11

His Arg Arg Cys Asn Lys Asn Asn Lys Lys Arg
1               5                   10

<210> SEQ ID NO 12
<211> LENGTH: 36
<212> TYPE: DNA
<213> ORGANISM: Artificial Sequence
<220> FEATURE:
<223> OTHER INFORMATION: DNA sequence for a candidate of ATF3 binding
      peptide

<400> SEQUENCE: 12
gttcctgatt tttatgctcc tactactagt cgttct                           36

<210> SEQ ID NO 13
<211> LENGTH: 36
<212> TYPE: DNA
<213> ORGANISM: Artificial Sequence
<220> FEATURE:
<223> OTHER INFORMATION: DNA sequence for a candidate of ATF3 binding
      peptide

<400> SEQUENCE: 13
gcgatgcctc ctacggatct tgagctgcat tcgaag                           36

<210> SEQ ID NO 14
<211> LENGTH: 36
<212> TYPE: DNA
<213> ORGANISM: Artificial Sequence
<220> FEATURE:
<223> OTHER INFORMATION: DNA sequence for a candidate of ATF3 binding
      peptide

<400> SEQUENCE: 14
catcctgctg ttccgggttc ttttctgaat tcggat                           36

<210> SEQ ID NO 15
<211> LENGTH: 36
<212> TYPE: DNA

<213> ORGANISM: Artificial Sequence
<220> FEATURE:
<223> OTHER INFORMATION: DNA sequence for a candidate of ATF3 binding peptide

<400> SEQUENCE: 15
gtgcttaata ttcctgagca ttttactgct cagaat                    36

<210> SEQ ID NO 16
<211> LENGTH: 36
<212> TYPE: DNA
<213> ORGANISM: Artificial Sequence
<220> FEATURE:
<223> OTHER INFORMATION: DNA sequence for a candidate of ATF3 binding peptide

<400> SEQUENCE: 16
catgggtttg agcagcattc gtttattatg aggttt                    36

<210> SEQ ID NO 17
<211> LENGTH: 36
<212> TYPE: DNA
<213> ORGANISM: Artificial Sequence
<220> FEATURE:
<223> OTHER INFORMATION: DNA sequence for a candidate of ATF3 binding peptide

<400> SEQUENCE: 17
acgcttggtc ttcgtccggt tcctgttgct actacg                    36

<210> SEQ ID NO 18
<211> LENGTH: 36
<212> TYPE: DNA
<213> ORGANISM: Artificial Sequence
<220> FEATURE:
<223> OTHER INFORMATION: DNA sequence for a candidate of ATF3 binding peptide

<400> SEQUENCE: 18
actatggtgc cggcgagttt ggttatgttt gagcgg                    36

<210> SEQ ID NO 19
<211> LENGTH: 36
<212> TYPE: DNA
<213> ORGANISM: Artificial Sequence
<220> FEATURE:
<223> OTHER INFORMATION: DNA sequence for a candidate of ATF3 binding peptide

<400> SEQUENCE: 19
atgcttgata ctaatattca gtctcggcct aatctt                    36

<210> SEQ ID NO 20
<211> LENGTH: 36
<212> TYPE: DNA
<213> ORGANISM: Artificial Sequence
<220> FEATURE:
<223> OTHER INFORMATION: DNA sequence for a candidate of ATF3 binding peptide

<400> SEQUENCE: 20
acgcttagtc tgccgggttt tactttgtt cctact                     36

<210> SEQ ID NO 21
<211> LENGTH: 36
<212> TYPE: DNA
<213> ORGANISM: Artificial Sequence
<220> FEATURE:
<223> OTHER INFORMATION: DNA sequence for a candidate of ATF3 binding
      peptide

<400> SEQUENCE: 21
gagacgaatc ttcttgatta tcctcgtatg gtgact                           36

<210> SEQ ID NO 22
<211> LENGTH: 36
<212> TYPE: DNA
<213> ORGANISM: Artificial Sequence
<220> FEATURE:
<223> OTHER INFORMATION: DNA sequence for a candidate of ATF3 binding
      peptide

<400> SEQUENCE: 22
aatacgccta ctcttgagcg taataagcat ctgtct                           36

<210> SEQ ID NO 23
<211> LENGTH: 36
<212> TYPE: DNA
<213> ORGANISM: Artificial Sequence
<220> FEATURE:
<223> OTHER INFORMATION: DNA sequence for a candidate of ATF3 binding
      peptide

<400> SEQUENCE: 23
aatgatgttg gtgtgctttc tcctgagact cggcag                           36

<210> SEQ ID NO 24
<211> LENGTH: 36
<212> TYPE: DNA
<213> ORGANISM: Artificial Sequence
<220> FEATURE:
<223> OTHER INFORMATION: DNA sequence for a candidate of ATF3 binding
      peptide

<400> SEQUENCE: 24
gctgagagtc cgttgactaa tcgtgggtgg aatcct                           36

<210> SEQ ID NO 25
<211> LENGTH: 12
<212> TYPE: PRT
<213> ORGANISM: Artificial Sequence
<220> FEATURE:
<223> OTHER INFORMATION: A candidate of ATF3 binding peptide

<400> SEQUENCE: 25

Val Pro Asp Phe Tyr Ala Pro Thr Thr Ser Arg Ser
1               5                   10

<210> SEQ ID NO 26
<211> LENGTH: 12
<212> TYPE: PRT
<213> ORGANISM: Artificial Sequence
<220> FEATURE:
<223> OTHER INFORMATION: A candidate of ATF3 binding peptide

<400> SEQUENCE: 26

Ala Met Pro Pro Thr Asp Leu Glu Leu His Ser Lys
1               5                   10

<210> SEQ ID NO 27
<211> LENGTH: 12
<212> TYPE: PRT
<213> ORGANISM: Artificial Sequence
<220> FEATURE:

<223> OTHER INFORMATION: A candidate of ATF3 binding peptide

<400> SEQUENCE: 27

His Pro Ala Val Pro Gly Ser Phe Leu Asn Ser Asp
1               5                   10

<210> SEQ ID NO 28
<211> LENGTH: 12
<212> TYPE: PRT
<213> ORGANISM: Artificial Sequence
<220> FEATURE:
<223> OTHER INFORMATION: A candidate of ATF3 binding peptide

<400> SEQUENCE: 28

His Gly Phe Glu Gln His Ser Phe Ile Met Arg Phe
1               5                   10

<210> SEQ ID NO 29
<211> LENGTH: 12
<212> TYPE: PRT
<213> ORGANISM: Artificial Sequence
<220> FEATURE:
<223> OTHER INFORMATION: A candidate of ATF3 binding peptide

<400> SEQUENCE: 29

Thr Met Val Pro Ala Ser Leu Val Met Phe Glu Arg
1               5                   10

<210> SEQ ID NO 30
<211> LENGTH: 12
<212> TYPE: PRT
<213> ORGANISM: Artificial Sequence
<220> FEATURE:
<223> OTHER INFORMATION: A candidate of ATF3 binding peptide

<400> SEQUENCE: 30

Thr Leu Ser Leu Pro Gly Phe Thr Phe Val Pro Thr
1               5                   10

<210> SEQ ID NO 31
<211> LENGTH: 12
<212> TYPE: PRT
<213> ORGANISM: Artificial Sequence
<220> FEATURE:
<223> OTHER INFORMATION: A candidate of ATF3 binding peptide

<400> SEQUENCE: 31

Glu Thr Asn Leu Leu Asp Tyr Pro Arg Met Val Thr
1               5                   10

<210> SEQ ID NO 32
<211> LENGTH: 12
<212> TYPE: PRT
<213> ORGANISM: Artificial Sequence
<220> FEATURE:
<223> OTHER INFORMATION: A candidate of ATF3 binding peptide

```
<400> SEQUENCE: 32

Asn Thr Pro Thr Leu Glu Arg Asn Lys His Leu Ser
1               5                   10

<210> SEQ ID NO 33
<211> LENGTH: 12
<212> TYPE: PRT
<213> ORGANISM: Artificial Sequence
<220> FEATURE:
<223> OTHER INFORMATION: A candidate of ATF3 binding peptide

<400> SEQUENCE: 33

Asn Asp Val Gly Val Leu Ser Pro Glu Thr Arg Gln
1               5                   10
```

PEPTIDE CAPABLE OF BINDING TO BIOMARKER FOR INFLAMMATORY AND METABOLIC DISEASES, AND USE THEREOF

TECHNICAL FIELD

The present invention relates to a novel peptide capable of binding to a biomarker of inflammatory and metabolic diseases and the use thereof, and more particularly to a peptide having ATF3-binding ability represented by one amino acid sequence selected from the group consisting of SEQ ID NOS: 1 to 4, a fusion peptide in which a peptide having cell permeability binds to the peptide having ATF3-binding ability, and the use of these peptides for the treatment of inflammatory diseases, metabolic diseases and/or autoimmune diseases.

BACKGROUND ART

ATF3 (activating transcription factor 3) protein is a component of the mammalian activation transcription factor/cAMP responsive element-binding (CREB) protein of transcription factors. ATF3 gene has been known to be expressed by various signals generated by various factors involved in cancer development, and to be involved in the complicated process of intracellular stress response.

ATF3 protein acts as an activator or repressor of known target genes, there are more than 20 potential target genes of ATF3 known in the literature to date, and known potential target genes of ATF3 include AdipoR1, AdipoR2, bNIP3, Cdc25A, CCL2, CCL4, Cyclin D1, FN-1, GLUT4, HIF-2α, IFN-γ, IL-1β, IL-6, IL-12b, IRS2, MMP1, MMP13, Noxa, p15PAF, Slug, Snail, STAT1, TNF-α, TWIST1, p53, p73, PDX-1, adiponectin, and the like.

In addition, various pathways such as NF-κB, JNK Erk, p38 and PKC induce ATF3 in most cells including fibroblasts and epithelial cells, as well as in immune cells such as macrophages, mast cells, T cells, and dendritic cells, and the induced ATF3 is involved in apoptosis, cell proliferation, cell motility, and DNA repair and metabolism by regulating the transcription of various genes. Among them, NF-κB is known to be associated with induction of related inflammatory reactions.

Currently, a great deal of research is underway on the association of the expression of ATF3 protein with inflammatory diseases (Lai P F et al., Evid.-Based Complement. Alternat. Med. 2013; 2013:716481), metabolic diseases such as obesity (Jang M K et al., Biochem. Biophys. Res. Commun. 2013 Feb. 15; 431(3):421-7), diabetes (KR 10-1652957), and cardiovascular diseases (Zhou H. et al., Basic Res. Cardiol. 2018 Aug. 9; 113(5):37), and autoimmune diseases (Smith C. K. et al., Ann. Rheum. Dis. 76 (2017) 602-611, Zheng S. et al., Mol. Cell. Biol., 33 (2013), 4857-4871). Substances that regulate the expression or function of ATF3 protein may inhibit the inflammatory response induced by ATF3, but effective inhibitors for ATF3 protein have not been developed to date.

Accordingly, as a result of extensive efforts to solve the problems with the prior art, the present inventors have developed a peptide that binds to ATF3, inhibits the expression of ATF3, and inhibits the signaling pathway of ATF3, and a pharmaceutical composition containing the same, and found that the peptide and the composition can reduce the production of inflammatory cytokines. Based on this finding, the present invention has been completed.

DISCLOSURE

Therefore, the present invention has been made in view of the above problems, and it is an object of the present invention to provide novel peptides capable of binding to ATF3 protein, a biomarker of inflammatory and metabolic diseases, and the uses thereof.

In accordance with one aspect of the present invention, the above and other objects can be accomplished by the provision of a peptide represented by any one amino acid sequence selected from the group consisting of SEQ ID NOS: 1 to 4, the peptide having the ability to bind to ATF3 protein.

In accordance with another aspect, provided is a fusion peptide comprising the peptide and a peptide represented by the amino acid sequence of SEQ ID NO: 5, binding to the N-terminus or C-terminus of the peptide.

In accordance with another aspect, provided is a pharmaceutical composition for the treatment of inflammatory diseases, metabolic diseases, autoimmune diseases and/or fibrotic diseases comprising the peptide or the fusion peptide as an active ingredient.

In accordance with another aspect, provided is the use of the peptide, the fusion peptide or the composition for the treatment of inflammatory diseases, metabolic diseases, autoimmune diseases and/or fibrotic diseases.

In accordance with another aspect, provided is the use of the peptide, the fusion peptide or the composition for the manufacture of a therapeutic drug for inflammatory diseases, metabolic diseases, autoimmune diseases and/or fibrotic diseases.

In accordance with another aspect, provided is a method for preventing and/or treating inflammatory diseases, metabolic diseases, autoimmune diseases and/or fibrotic diseases comprising administering the peptide, the fusion peptide or the composition to a subject in need of treatment of the inflammatory diseases, metabolic diseases, autoimmune diseases and/or fibrotic diseases.

BEST MODE

Unless defined otherwise, all technical and scientific terms used herein have the same meanings as appreciated by those skilled in the field to which the present invention pertains. In general, the nomenclature used herein is well-known in the art and is ordinarily used.

In the present invention, sequences of peptides having ATF3-binding ability, which is a biomarker of inflammatory and metabolic diseases, were discovered using a phage display method, and the peptides were found to have ATF3-binding ability in a concentration-dependent manner.

Accordingly, in one aspect, the present invention is directed to a peptide capable of binding to ATF3 protein.

The peptide may be represented by any one amino acid sequence selected from the group consisting of SEQ ID NOS: 1 to 4.

```
(ABP1):
                                   SEQ ID NO: 1
AESPLTNRGWNP (ABP2):
                                   SEQ ID NO: 2
MLDTNIQSRPNL (ABP3):
                                   SEQ ID NO: 3
TLGLRPVPVATT (ABP4):
                                   SEQ ID NO: 4
VLNIPEHFTAQN
```

In the present invention, the peptide having the ability to bind to ATF protein may be represented by any one amino acid sequence selected from the group consisting of SEQ ID NOS: 1 to 4, and may have a homology of 60% or more, 70% or more, 80% or more, 90% or more, or 95% or more with the amino acid sequence. It will be obvious to those skilled in the art that any one amino acid sequence selected from the group consisting of SEQ ID NOS: 1 to 4 may be appropriately substituted to accomplish the object of the present invention; for example, some amino acids (for example, 1 to 5 amino acids) in the amino acid sequence of the peptides of SEQ ID NOS: 1 to 4 may be substituted with other amino acids, or some amino acids (for example, 1 to 5 amino acids) in the amino acid sequence of the peptides of SEQ ID NOS: 1 to 4 may be added or deleted, if an advantageous effect on the stability of the peptide is provided without affecting the desired structure or function of the peptide.

The present invention is based on the finding that the peptides of SEQ ID NOS: 1 to 4 have low cell permeability, whereas the peptides of SEQ ID NOS: 6 to 9, obtained by binding the peptide of each of SEQ ID NOS: 1 to 4 to the peptide of SEQ ID NO: 5, having cell permeability, have improved cell permeability.

Accordingly, in another aspect, the present invention is directed to a fusion peptide having cell permeability as well as ATF3-binding ability.

The fusion peptide may have a structure in which the peptide having cell permeability binds to the peptide of each of SEQ ID NOS: 1 to 4, and the peptide having cell permeability may be a peptide having an amino acid sequence of SEQ ID NO: 5, SEQ ID NO: 10, or SEQ ID NO: 11.

In the present invention, the peptide having cell permeability may be represented by an amino acid sequence of SEQ ID NO: 5, SEQ ID NO: 10, or SEQ ID NO: 11, or may have a homology of 60% or more, 70% or more, 80% or more, 90% or more, or 95% or more with the amino acid sequence. It will be obvious to those skilled in the art that the amino acid sequence of SEQ ID NO: 5, SEQ ID NO: 10, or SEQ ID NO: 11 may be appropriately substituted to accomplish the object of the present invention; for example, some amino acids (for example, 1 to 5 amino acids) in the amino acid sequence of the peptide of SEQ ID NO: 5, SEQ ID NO: 10, or SEQ ID NO: 11 may be substituted with other amino acids, or some amino acids (for example, 1 to 5 amino acids) in the amino acid sequence of the peptide of SEQ ID NO: 5, SEQ ID NO: 10, or SEQ ID NO: 11 may be added or deleted, if an advantageous effect on the stability of the peptide is provided without affecting the desired structure or function of the peptide.

Meanwhile, the fusion peptide may be represented by any one amino acid sequence selected from the group consisting of SEQ ID NOS: 6 to 9.

```
(hBD-3-3):
                                   SEQ ID NO: 5
GKCSTRGRKCCRRKK (ABP1-hBD3-3):
                                   SEQ ID NO: 6
AESPLTNRGWNPGKCSTRGRKCCRRKK (ABP2-hBD3-3):
                                   SEQ ID NO: 7
MLDTNIQSRPNLGKCSTRGRKCCRRKK (ABP3-hBD3-3):
                                   SEQ ID NO: 8
TLGLRPVPVATTGKCSTRGRKCCRRKK (ABP4-hBD3-3):
                                   SEQ ID NO: 9
VLNIPEHFTAQNGKCSTRGRKCCRRKK (LMWP):
                                   SEQ ID NO: 10
VSRRRRRGGRRRR (H4):
                                   SEQ ID NO: 11
HRRCNKNNKKR
```

The fusion peptide may be synthesized by linking a peptide represented by the amino acid sequence of SEQ ID NO: 5, SEQ ID NO: 10, or SEQ ID NO: 11 to the C-terminal of the peptide represented by the amino acid sequence of each of SEQ ID NO: 1 to SEQ ID NO: 4, or may also be synthesized by linking a peptide represented by the amino acid sequence of SEQ ID NO: 5, SEQ ID NO: 10, or SEQ ID NO: 11 to the N-terminal of the peptide represented by the amino acid sequence of each of SEQ ID NOS: 1 to 4.

In addition, the peptide represented by the amino acid sequence of each of SEQ ID NOS: 1 to 4 may be linked to the peptide represented by the amino acid sequence of SEQ ID NO: 5, SEQ ID NO: 10, or SEQ ID NO: 11 by a linker. Any linker may be used as the linker, as long as it can provide an area where each peptide can form a functional structure. For example, the linker may be a peptidic linker which is naturally derived and/or synthesized. The naturally derived and/or synthetic peptidic linker may have an amino acid chain consisting of 1 to 50 amino acids, and may include a sequence of repeating amino acids of naturally occurring polypeptides, such as polypeptides having a hinge function. In another embodiment, the peptidic linker amino acid sequence may be a synthetic linker amino acid sequence designed to be rich in glycine, glutamine, and/or serine residues. For example, these residues may be arranged in small repeating units of 5 or fewer amino acids, and the small repeating units may be arranged repeatedly to form a multimer unit. 6 or fewer additional optional naturally occurring amino acids may be added at the amino- and/or carboxy terminus of the multimer unit. Other synthetic peptidic linkers may have a single configuration of amino acids repeated 10 to 20 times, and may have 6 or fewer additional optional naturally occurring amino acids at the amino- and/or carboxy-terminus. Meanwhile, the linker may be in the form of a chemically modified amino acid. For example, Fmoc-6-aminohexanoic acid (Fmoc-ε-Acp-OH), to which Fmoc-(9-fluorenylmethoxycarbonyl) binds, may be used as a blocking group, but is not limited thereto.

A part of the peptides of SEQ ID NOS: 1 to 4 can pass through cells, but the cell permeability thereof is found to be not excellent. However, when linking the peptide of SEQ ID NO: 5, having cell permeability, to each of the peptides of SEQ ID NOS: 1 to 4, the cell permeability of the peptides of SEQ ID NOS: 1 to 4 increases, thus the peptide can bind more easily to the ATF3 protein in the cell since the ATF3 protein is present in the cell. Therefore, the effect of acting on ATF3 can be increased.

ATF3 is known to be an important factor in inflammatory diseases, metabolic diseases, autoimmune diseases and fibrotic diseases.

Thus, in another aspect, the present invention is directed to a pharmaceutical composition for treating an inflammatory disease comprising the peptide or the fusion peptide as an active ingredient.

In the present invention, the inflammatory disease may comprise at least one selected from the group consisting of arthritis, periodontitis, atopy, thyroiditis, uveitis, Hashimoto's thyroiditis, gastritis, steatohepatitis, hepatitis and enteritis, but is not limited thereto.

In another aspect, the present invention is directed to a pharmaceutical composition for treating a metabolic disease comprising the peptide or the fusion peptide as an active ingredient.

In the present invention, the metabolic disease comprises at least one selected from the group consisting of obesity, weight loss, diabetes, atherosclerosis, arteriosclerosis, cardiovascular diseases, neurological diseases, Alzheimer's disease, cognitive impairment, oxidative stress, skin diseases, skin aging, damage caused by UV irradiation, hypertension, hypercholesterolemia, hyperlipidemia, immunodeficiency, cancer and metabolic syndrome, but is not limited thereto.

In the present invention, the term "hypercholesterolemia" refers to a condition characterized by higher concentrations of LDL, HDL and/or VLDL in the blood than normal, and the term "hyperlipidemia" refers to a condition characterized by higher concentrations of triglyceride than normal.

In another aspect, the present invention is directed to a pharmaceutical composition for treating an autoimmune disease comprising the peptide or the fusion peptide as an active ingredient.

In the present invention, the autoimmune disease comprises at least one selected from the group consisting of insulin-dependent diabetes, multiple sclerosis, autoimmune encephalomyelitis, rheumatoid arthritis, osteoarthritis, myasthenia gravis, thyroiditis, uveitis, Hashimoto's thyroiditis, thyroid toxicosis, pernicious anemia, autoimmune atrophy gastritis, autoimmune hemolytic anemia, idiopathic leukopenia, primary sclerosing cholangitis, alcoholic/non-alcoholic steatohepatitis, inflammatory bowel disease, Crohn's disease, ulcerative bowel disease, psoriasis, Sjogren's syndrome, scleroderma, Wegener's granulomatosis, polymyositis, dermatomyositis, discoid LE and systemic lupus erythematosus, but is not limited thereto.

In another aspect, the present invention is directed to a pharmaceutical composition for treating a fibrotic disease comprising the peptide or the fusion peptide as an active ingredient.

In the present invention, the fibrotic disease may include at least one selected from the group consisting of cirrhosis caused by fibrosis, pulmonary fibrosis, obstructive pulmonary disease, heart failure, arteriosclerosis, chronic kidney failure, diabetes, and keloids caused by postoperative sequelae, but is not limited thereto.

In another aspect, the present invention is directed to the use of the peptide, the fusion peptide, or the composition for the treatment of inflammatory diseases.

In another aspect, the present invention is directed to the use of the peptide, the fusion peptide or the composition for the treatment of metabolic diseases.

In another aspect, the present invention is directed to the use of the peptide, the fusion peptide or the composition for the treatment of autoimmune diseases.

In another aspect, the present invention is directed to the use of the peptide, the fusion peptide or the composition for the treatment of fibrotic diseases.

In another aspect, the present invention is directed to the use of the peptide, the fusion peptide or the composition in the manufacture of a medicine for treating inflammatory diseases.

In another aspect, the present invention is directed to the use of the peptide, the fusion peptide or the composition in the manufacture of a medicine for treating metabolic diseases.

In another aspect, the present invention is directed to the use of the peptide, the fusion peptide or the composition in the manufacture of a medicine for treating autoimmune diseases.

In another aspect, the present invention is directed to the use of the peptide, the fusion peptide or the composition in the manufacture of a medicine for treating fibrotic diseases.

In another aspect, the present invention is directed to a method for preventing and treating inflammatory diseases, comprising administering the peptide, the fusion peptide or the composition to a subject in need of treatment of an inflammatory disease.

In another aspect, the present invention is directed to a method for preventing and treating metabolic diseases, comprising administering the peptide, the fusion peptide or the composition to a subject in need of treatment of a metabolic disease.

In another aspect, the present invention is directed to a method for preventing and treating autoimmune diseases, comprising administering the peptide, the fusion peptide or the composition to a subject in need of treatment of an autoimmune diseases.

In another aspect, the present invention is directed to a method for preventing and treating fibrotic diseases, comprising administering the peptide, the fusion peptide or the composition to a subject in need of treatment of a fibrotic diseases.

The pharmaceutical composition of the present invention may further comprise at least one pharmaceutically acceptable carrier in addition to the peptide. The pharmaceutically acceptable carrier may be saline, sterile water, Ringer's solution, buffered saline, dextrose solution, maltodextrin solution, glycerol, ethanol, and a combination of one or more of these components. If necessary, other conventional additives such as antioxidants, buffers and bacteriostatic agents may be added. In addition, diluents, dispersants, surfactants, binders and lubricants may be further added to prepare injectable formulations such as aqueous solutions, suspensions and emulsions, as well as pills, capsules, granules or tablets.

Therefore, the composition of the present invention is prepared in any one formulation selected from the group consisting of injections, formulations for oral administration, patches, solutions, capsules, granules, tablets, powders, sprays, ointments, gels, mucosal formulations and suppositories, but is not limited thereto. These formulations can be prepared by a conventional method used for formulation in the art or by a method disclosed in Remington's Pharmaceutical Science (latest edition), Mack Publishing Company, Easton Pa., and can be prepared in various formulations depending on each disease or component.

The therapeutic pharmaceutical composition may be formulated such that it additionally contains a pharmaceutically acceptable adjuvant, and the pharmaceutically acceptable adjuvant may include at least one selected from the group consisting of excipients, diluents, buffers, antimicrobial preservatives, surfactants, antioxidants, thickeners and viscosity modifiers, but is not limited thereto.

The composition of the present invention may be administered orally or parenterally (for example, intravenous, subcutaneous, intraperitoneal or topical application) according to a desired method, and the dose may be varied depending on the patient's weight, age, gender, state of health, diet, administration time, administration method, excretion rate, and disease severity. When the peptides of SEQ ID NOS: 1 to 9 of the present invention are used for the treatment of inflammatory diseases, metabolic diseases, autoimmune diseases, and/or fibrotic diseases, the daily dose of the peptides is about 1 to about 100 mg/kg, preferably 5 to 50 mg/kg, and may be administered once a day or 2 to 3 times a week, but is not limited thereto.

In this case, the administration regimen and dose vary depending on the age, weight and response of an individual patient. A suitable regimen and dosage can be easily selected by those skilled in the art who take these factors into consideration.

EXAMPLE

Hereinafter, the present invention will be described in more detail with reference to examples. However, it will be obvious to those skilled in the art that these examples are provided only for illustration of the present invention and should not be construed as limiting the scope of the present invention.

Example 1: Discovery of Peptides Having ATF3 Protein-Binding Ability

Example 1-1: Search of Peptide Sequence Having ATF3-Binding Ability Using Phage Display Phage display was used to find a specific peptide sequence that binds to ATF3. After M13 phages labeled with a random peptide library with high diversity and complexity were adhered to a polystyrene plate well of a coated with the ATF3 protein, the suspended phages were washed out to collect only adherent phages. This process was repeated several times. A peptide sequence having ATF3-binding ability was found by sequencing the DNA encoding the peptide labeled on the finally obtained phages using subtractive panning. Subtractive panning is a novel phage display method that can be used to find a sequence that binds to a specific substance, but does not bind to other substances.

The phage display kit used herein was a Ph.D.-12 Phage Display Kit (New England Biolabs (USA)), and the final 17 clones in the form of *E. coli* culture, found using phages labeled with a random peptide library consisting of 12 amino acids provided in the kit, were sequenced by Cosmo Genetech Co., Ltd.

As shown in Table 1, as a result, four sequences in which two clones have the identical DNA sequence were identified, and it was possible to obtain the sequences of the final peptides consisting of 12 amino acids: SEQ ID NO: (ABP1, AESPLTNRGWNP), SEQ ID NO: 2 (ABP2 (MLDTNIQSRPNL), SEQ ID NO: 3 (ABP3, TLGLRPVPVATT), and SEQ ID NO: 4 (ABP3, VLNIPEHFTAQN) by translating the same. The peptide sequences are likely to be specific sequences that bind to ATF3, and were thus selected as candidates for a specific peptide sequence for binding to ATF3.

TABLE 1

| Clone | DNA sequence | SEQ ID NO. of DNA sequence | Amino acid sequence | SEQ ID NO. of Amino acid sequence |
|---|---|---|---|---|
| #1 | 5'-GTT CCT GAT TTT TAT GCT CCT ACT ACT AGT CGT TCT-3' | 12 | VPDFYA PTTSRS | 25 |
| #2 | 5'-GCG ATG CCT CCT ACG GAT CTT GAG CTG CAT TCG AAG-3' | 13 | AMPPTD LELHSK | 26 |
| #3 | 5'-CAT CCT GCT GTT CCG GGT TCT TTT CTG AAT TCG GAT-3' | 14 | HPAVPGS FLNSD | 27 |
| #4 | 5'-GTG CTT AAT ATT CCT GAG CAT TTT ACT GCT CAG AAT-3' | 15 | VLNIPEH FTAQN | 4 |
| #5 | 5'-GTG CTT AAT ATT CCT GAG CAT TTT ACT GCT CAG AAT-3' | 15 | VLNIPEH FTAQN | 4 |
| #6 | 5'-CAT GGG TTT GAG CAG CAT TCG TTT ATT ATG AGG TTT-3' | 16 | HGFEQHS FIMRF | 28 |
| #7 | 5'-ACG CTT GGT CTT CGT CCG GTT CCT GTT GCT ACT ACG-3' | 17 | TLGLRPV PVATT | 3 |
| #8 | 5'-ACG CTT GGT CTT CGT CCG GTT CCT GTT GCT ACT ACG-3' | 17 | TLGLRPV PVATT | 3 |
| #9 | 5'-ACT ATG GTG CCG GCG AGT TTG GTT ATG TTT GAG CGG-3' | 18 | TMVPAS LVMFER | 29 |
| #10 | 5'-ATG CTT GAT ACT AAT ATT CAG TCT CGG CCT AAT CTT-3' | 19 | MLDTNI QSRPNL | 2 |

TABLE 1-continued

| Clone | DNA sequence | SEQ ID NO. of DNA sequence | Amino acid sequence | SEQ ID NO. of Amino acid sequence |
|---|---|---|---|---|
| #11 | 5'-ATG CTT GAT ACT AAT ATT CAG TCT CGG CCT AAT CTT-3' | 19 | MLDTNI QSRPNL | 2 |
| #12 | 5'-ACG CTT AGT CTG CCG GGT TTT ACT TTT GTT CCT ACT-3' | 20 | TLSLPG FTFVPT | 30 |
| #13 | 5'-GAG ACG AAT CTT CTT GAT TAT CCT CGT ATG GTG ACT-3' | 21 | ETNLLD YPRMVT | 31 |
| #14 | 5'-AAT ACG CCT ACT CTT GAG CGT AAT AAG CAT CTG TCT-3' | 22 | NTPTLE RNKHLS | 32 |
| #15 | 5'-AAT GAT GTT GGT GTG CTT TCT CCT GAG ACT CGG CAG-3' | 23 | NDVGVL SPETRQ | 33 |
| #16 | 5'-GCT GAG AGT CCG TTG ACT AAT CGT GGG TGG AAT CCT-3' | 24 | AESPLT NRGWNP | 1 |
| #17 | 5'-GCT GAG AGT CCG TTG ACT AAT CGT GGG TGG AAT CCT-3' | 24 | AESPLT NRGWNP | 1 |

Example 1-2: Synthesis of Peptide Having ATF3-Binding Ability

Peptides of SEQ ID NOS: 1 to 4 in order from the N-terminus were synthesized using F-moc solid phase peptide synthesis. The synthesized peptide sequences were cut from the resin, washed, lyophilized and then separated and purified by liquid chromatography. The molecular weight of the purified peptide was determined using MALDI-TOF analysis.

Example 1-3: Determination of Binding Affinity of Peptide Having ATF3-Binding Ability to ATF3 Protein Biotin was labeled on the peptide of Example 1-2 to determine the binding affinity of the peptide to the ATF3 protein. Each peptide was biotinylated using EZ-link sulfo-NHS-biotin (Pierce Biotechnology, USA) in accordance with the manufacturer's instructions, and unbound byproducts were removed using ultrafiltration, which is a membrane separation method using pressure difference as a driving force. Then, the molecular weight of the synthetic product was detected by measuring the molecular weight using mass spectrometry. Analysis and purification were performed using analytic reverse-phase liquid chromatography. The analysis was performed by flowing 0.1% TFA/$H_2O$ and 0.092% TFA/acetonitrile with gradient from 0 to 60% at a flow rate of 1 ml/min using a 4.6 mm diameter $C_{18}$ column for 30 minutes. At this time, the wavelength of the ultraviolet detector was 220 nm. The purification was carried out using a column having a diameter of 2.2 cm at a flow rate of 20 ml/min under the same solvent and detection wavelength conditions as above. The solvent was removed from a part of the biotin-conjugated peptide using a rotary evaporator, and was then freeze-dried.

The binding affinity of the peptide having ATF3-binding ability to the ATF3 protein was measured using an avidin-biotin complex binding assay. Each well of a 96-well polystyrene plate was coated with ATF3 protein at a concentration of 0.02 μg/μl for 16 hours, and was then blocked with a blocking solution (0.1 M $NaHCO_3$ (pH 8.6), 5 mg/ml BSA, 0.02% $NaN_3$ (optional), filter sterilized) for at least 1 hour, and the blocking solution was discarded and strongly washed 6 or more times with a washing solution (TBS+0.1% [v/v] Tween-20). Then, the peptides of SEQ ID NOS: 1 to 4 (ABP1-4), namely, the peptides with ATF3-binding ability, which have been biotin-labeled and obtained by conducting synthesis, separation and purification, were seeded on the surface of the wells coated with ATF3 protein in an amount of 150 μl at various concentrations from 10 μM to 100 μM. After conducting reaction at room temperature for 2 hours, the resulting product was washed vigorously at least 6 times with a washing solution suitable for each, and 150 μl of a dilution of ExtrAvidin-Peroxidase (Cat. #E2886, Sigma-Aldrich, USA) to 1:500 in blocking solution was seeded into each well. After conducting reaction at room temperature for 1 hour, the resulting product was washed 6 or more times strongly with an appropriate washing solution, 150 μl of a substrate solution (2,2'-AZINO-BIS, Cat. #A3219, Sigma-Aldrich, USA) was seeded to the well, and color development was performed at room temperature for 20 minutes. After 20 minutes, the resulting product was treated with 50 μl of a 1% SDS solution in order to stop the reaction, and absorbance was measured at 405 nm.

Figures 1, 2:
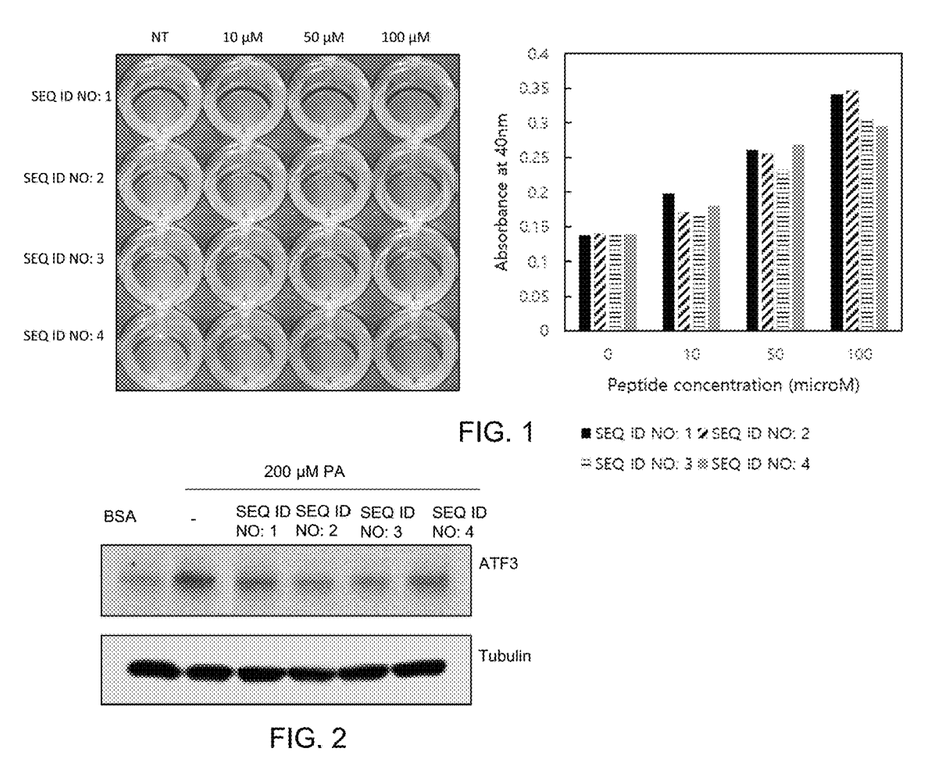
FIG. 1 shows binding of peptides of SEQ ID NOS: 1 to 4 to an ATF3 protein in a concentration-dependent manner.
FIG. 2 is a result of Western blot for detecting the amount of ATF3 protein upon treatment with the peptides of SEQ ID NOS: 1 to 4.

As a result, as can be seen from FIG. 1, when the ATF3 protein was treated with the peptide having ATF3-binding ability of Example 1-2, the tendency of the peptide to bind the ATF3 protein in a concentration-dependent manner was determined.

Example 2: Peptide with Cell Permeability and ATF3-Binding Ability

The peptide of each of SEQ ID NOS: 6 to 9 was synthesized by F-moc solid phase peptide synthesis by ligating the peptide of SEQ ID NO: 5 to the C-terminus of the peptide of each of SEQ ID NO: 1 to 4, having ATF3 protein-binding ability. The synthesized peptide sequence was cut from resin, washed, lyophilized, and separated and purified by liquid chromatography. The molecular weight of the purified peptide was determined using MALDI-TOF analysis.

Example 3: Determination of Peptide Effect in Non-Alcoholic Steatohepatitis Animal Model A methionine-choline deficient (MCD) diet was fed to C57BL/6J mice for 8 weeks to induce a non-alcoholic fatty liver model, SEQ ID NO: 1 peptide was administered thereto at each dose for 6 weeks and then the effect was evaluated.

Example 4: Determination of Peptide Effect in Inflammatory Bowel Disease Animal Model The therapeutic effect was determined by inducing inflammatory bowel disease using a solution of drinking water in 5% DSS in ICR mice for 10 days while administering peptides to the mice.

Experimental Example 1: Determination of Effect of ATF3-Binding Peptide on Reduction of Expression of ATF3 Protein, Liver Disease Marker Western blot was performed to determine the effects of the peptides of SEQ ID NOS: 1 to 4 on the change in the expression of the ATF3 protein. HepG2 cells were plated at a density of 70% on a 6-well plate. 16 hours later, the cells were starved with DMEM medium containing 0.5% FBS for 2 hours. The cells were treated with a medium containing each of the peptides of SEQ ID NOS: 1 to 4 at a concentration of 200 μM for 2 hours, and were then treated with palmitic acid at a concentration of 200 μM for 24 hours to induce an inflammatory response. Cells were lysed using RIPA lysis buffer (25 mM Tris.HCl pH 7.6, 150 mM NaCl, 1% NP-40, 1% sodium deoxycholate, 0.1% SDS) containing a protease inhibitor and a phosphatase inhibitor. Proteins were assayed through BCA protein assay, and expression levels of ATF3 and tubulin proteins were detected by western blot. Western blot was conducted by loading an equal amount of each sample along with a size marker on an 8% SDS PAGE gel, followed by electrophoresis for about 2 hours and transfer to a nitrocellulose membrane. The transferred membrane was blocked with 5% skim milk for 1 hour, and was reacted with the primary antibody overnight at a ratio of 1:1000. Then, the membrane was washed with TBST containing 0.1% tween-20 and reacted with a secondary antibody to which HRP was adhered for 1 hour, and then chemiluminescence was detected with an ECL substrate.

As a result, as shown in FIG. 2, when treated with palmitic acid alone, the expression of ATF3 protein, which is a liver disease marker, was increased, but when treated with a combination of the palmitic acid with peptides of SEQ ID NOS: 1 to 4, the expression of the ATF3 protein was found to decrease. This indicates that the peptides of SEQ ID NOS: 1 to 4 have an effect of inhibiting the expression of ATF3 protein, which is a liver disease marker, and that the peptides of SEQ ID NOS: 1 to 4 have an effect of treating liver diseases.

Experimental Example 2: Determination of Effect of SEQ ID NO: 5 on Increase in Cell Permeability of Peptide Having ATF3 Protein-Binding Ability RAW 264.7 cells were seeded at a density of $2\times10^4$/well on a 6-well plate. After 24 hours, replacement was conducted with DMEM medium containing 0.5% FBS. The cells were treated with 50 μM of each of fluorescence (rhodamine)-labeled peptides of SEQ ID NOS: 1, 5 and 6. After 20 minutes, the cells were fixed and observed with a confocal microscope.

Figure 3:
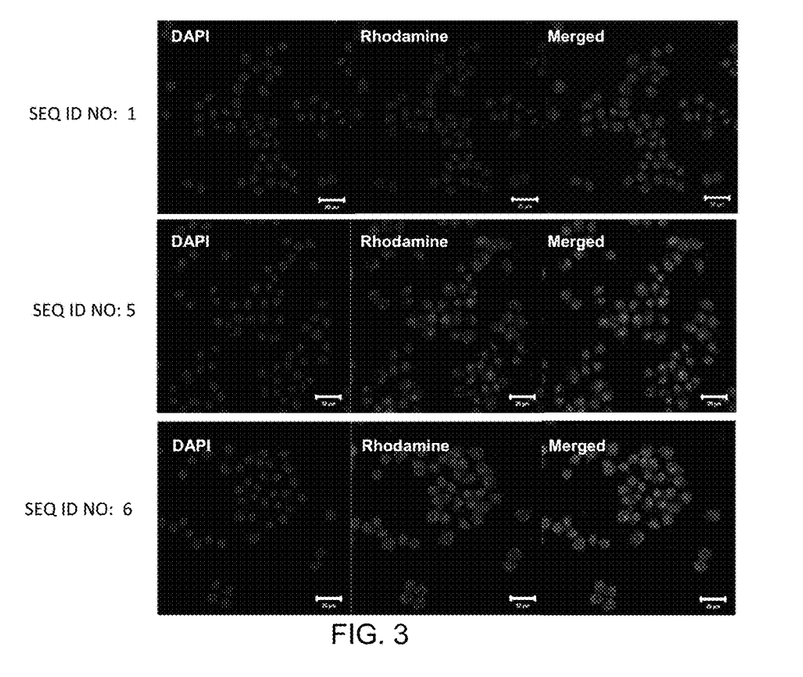
FIG. 3 is a confocal micrograph image showing the cell permeability of the peptides of SEQ ID NO: 1, SEQ ID NO: 5, and SEQ ID NO. 6.

As a result, as can be seen from FIG. 3, the peptide of SEQ ID NO: 1 has a slightly red fluorescence in the cells, indicating that some of the cells were permeated, and the peptides of SEQ ID NO: 5 and SEQ ID NO: 6 had more fluorescence in the cells than the peptide of SEQ ID NO: 1, indicating that the peptides of SEQ ID NO: 5 and SEQ ID NO: 6 had excellent cell permeability.

This means that, by binding the peptide of SEQ ID NO: 5, having high cell permeability, to the peptide of SEQ ID NO: 1, having low cell permeability the intracellular permeability of the peptide capable of binding to the ATF3 protein (i.e., SEQ ID NO: 6) can be further increased, and the effect in the cells can be improved.

Experimental Example 3: Determination of Effect of ATF3-Binding Peptide on Reduction of Expression of IL-6

HepG2 cells were plated at a density of 70% on a 6-well plate. After 16 hours, the cells were starved using DMEM medium containing 0.5% FBS for 2 hours. The cells were treated with a medium containing each of the peptides of SEQ ID NOS: 1 to 6 at a concentration of 200 μM for 2 hours, and were further treated with palmitic acid at a concentration of 200 μM to induce an inflammatory response for 24 hours. Each medium was collected, and the level of expression of IL-6, an inflammatory cytokine, was detected with an ELISA kit (R&D, Minneapolis, Minn., USA).

Figure 4:
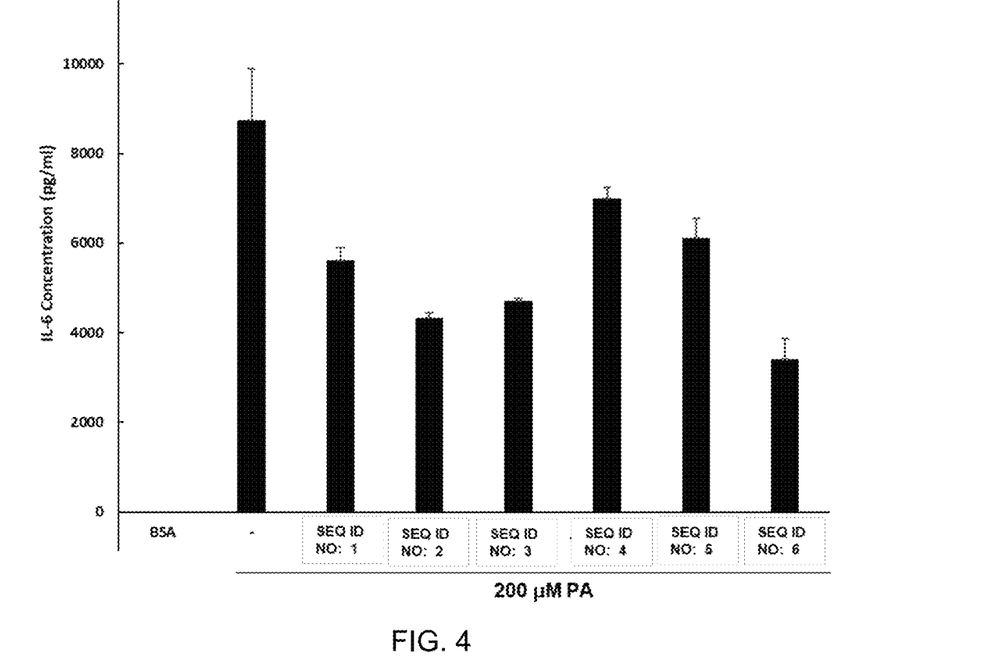
FIG. 4 shows a result of ELISA for detecting the expression level of IL-6 upon treatment with the peptides of SEQ ID NOS: 1 to 6.

As a result, as can be seen from FIG. 4, the amount of expression of IL-6, increased by palmitic acid, was reduced by the ATF3-binding peptide. This proves that the ATF3-binding peptide is effective in treating liver diseases by reducing the production of cytokines that cause inflammation. In addition, SEQ ID NO: 6 had the lowest IL-6 expression level, which indicates that the inhibitory effect of cytokine expression was further increased by the cell permeability of SEQ ID NO: 5.

Experimental Example 4: Determination of Peptide Effect in Non-Alcoholic Steatohepatitis Animal Model An MCD mouse model was used to determine whether or not the peptide is effective in treating steatohepatitis at the animal level according to the present invention. Male C57BL/6J mice were used and fed a normal diet, an MCD diet, a low dose of SEQ ID NO: 1 peptide (20 mg/kg) with MCD diet, and a high dose of SEQ ID NO: 1 peptide (80 mg/kg) with MCD diet. A MCD diet was freely fed to the mice for 8 weeks and then the peptides were administered thereto once a day, or every three days a total of 12 times. For all animals, body weight was measured immediately before the start of administration and twice weekly throughout the experiment. After the completion of the last administration, blood was collected from the subject through the postcaval vein under respiratory anesthesia with isoflurane, and then the subject was subjected to euthanasia by bloodletting. After euthanasia, the appearance was visually observed, and the characteristics of the organs in the abdominal cavity and thoracic cavity were observed. For all animals subjected to autopsy, tissues were fixed in a neutral buffered formalin solution, and paraffin blocks were prepared by tissue processing and sliced into microsections. The tissue sections were subject to H&E staining (FIG. 5A), Sirius red staining (FIG. 5B), and Masson trichrome staining (FIG. 5C) to detect the degree of fat accumulation and fibrosis in liver tissue.

Figure 5A:
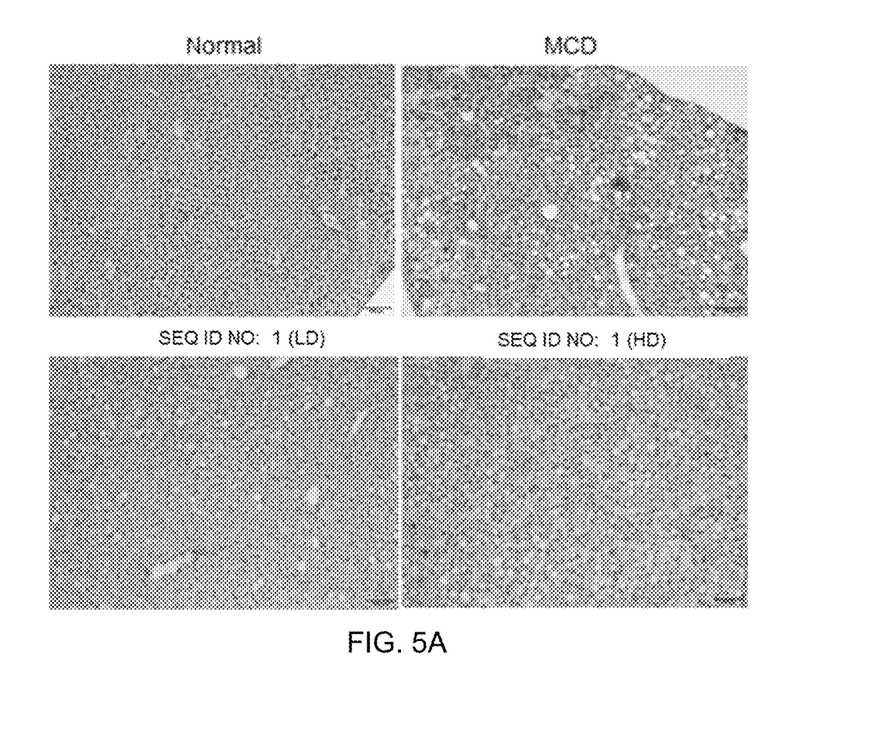
FIG. 5A shows the result of H&E staining for detecting reduction of liver tissue inflammation and fat in a non-alcoholic steatohepatitis animal model upon treatment with the peptide of SEQ ID NO: 1.
Figure 5B:
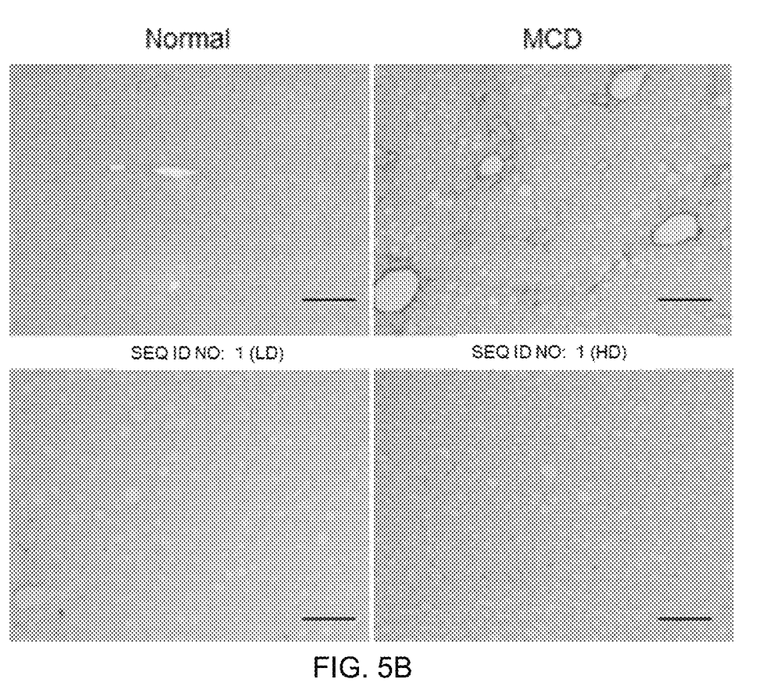
FIG. 5B shows a result of Sirius red staining for detecting the effect of reducing fibrosis in liver tissue in a non-alcoholic steatohepatitis animal model upon treatment with the peptide of SEQ ID NO: 1.
Figure 5C:
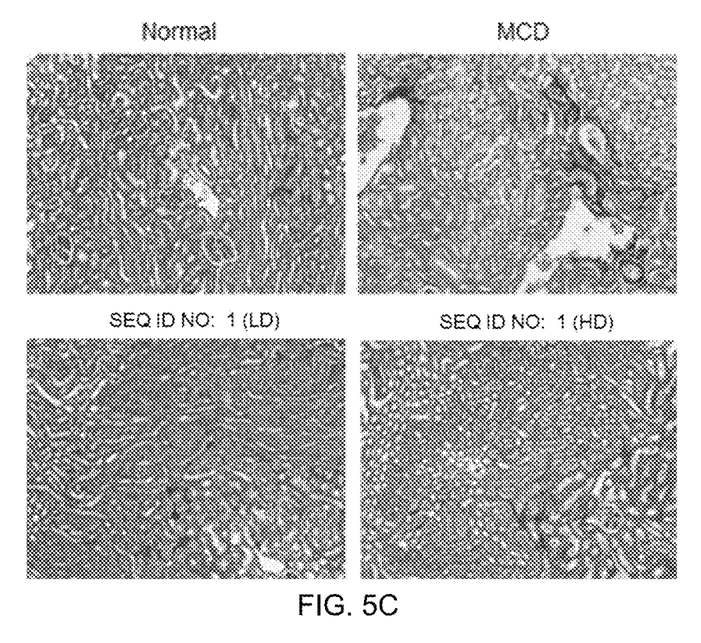
FIG. 5C shows the result of Masson trichrome staining for detecting the effect of reducing fibrosis in liver tissue in a non-alcoholic steatohepatitis animal model upon treatment with the peptide of SEQ ID NO: 1.

As a result, as can be seen from FIG. 5A, the number and size of inflammation and fat particles increased in the MCD diet-fed group, whereas the number and size of inflammation and fat particles decreased in the group injected with the SEQ ID NO: 1 peptide. As can be seen from FIGS. 5B and 5C, fibrosis was very severe in the MCD-diet-fed group (red in FIG. 5B, and blue in FIG. 5C), and fibrosis was significantly reduced in the group injected with SEQ ID NO: 1 peptide.

Figure 5D:
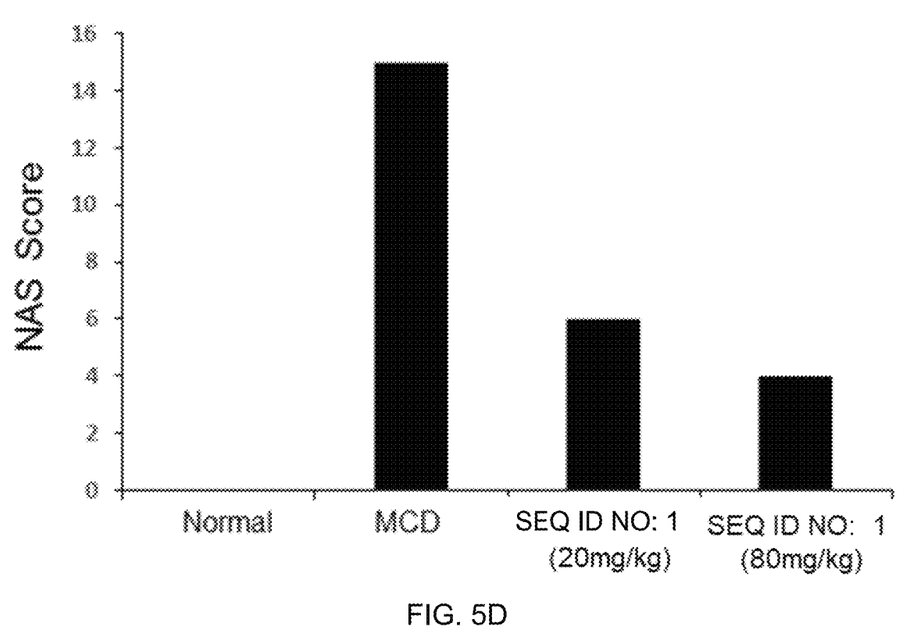
FIG. 5D shows the result of measurement of NAS scores for each group in the non-alcoholic steatohepatitis animal model administered with the peptide of SEQ ID NO: 1.

The NAS score is an index of the sum of ballooning degeneration, lobular inflammation and steatosis. The NAS score was reduced by 50% or more in the peptide-treated group, indicating that non-alcoholic fatty liver was ameliorated (FIG. 5D).

Experimental Example 5: Determination of Peptide Effect in Inflammatory Bowel Disease Animal Model Whether or not the peptide has a therapeutic effect in the animal-level inflammatory bowel disease model according to the present invention was determined. ICR mice were used and the peptide was injected through IP injection while inducing inflammation using 5% DSS as drinking water for 10 days to induce inflammation. Each of normal, defective, positive control (SAHA), immunomodulatory control (anti-TNF-a antibody) and SEQ ID NO: 1 peptide treatment was conducted daily for 10 days. After 10 days, the mice were sacrificed by $CO_2$ hyperventilation, the colon and spleen were collected, and whether or not intestinal villi were damaged was determined through colon length and H&E staining using paraffin production (FIG. 6).

Figure 6:
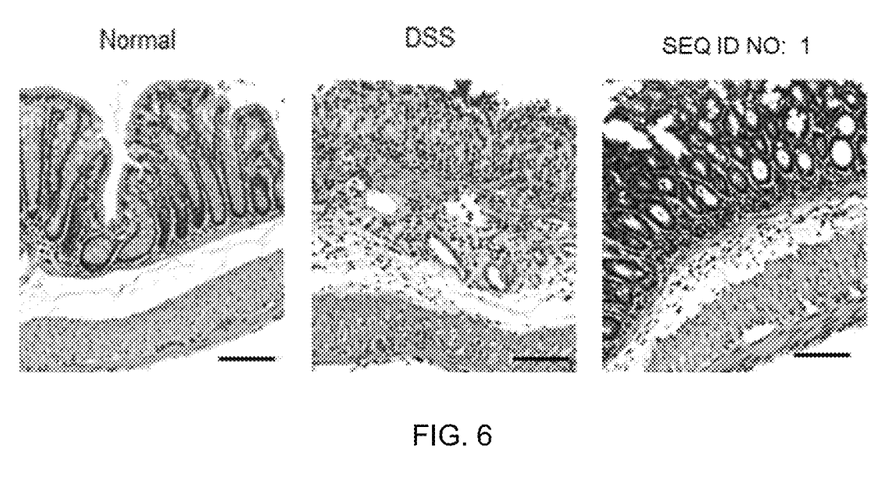
FIG. 6 shows a result of H&E staining for observing the intestinal villi after treatment of an inflammatory bowel disease animal model with the peptide of SEQ ID NO: 1.

As a result, as can be seen from FIG. 6, more inflammatory cells were observed and villi were severely damaged in the DSS-induced group. In the group treated with the SEQ ID NO: 1 peptide, the number of inflammatory cells was reduced and the villi were preserved without damage.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

INDUSTRIAL APPLICABILITY

The present invention provides a novel peptide having the ability to bind to ATF3, which is a protein that acts as an important factor in the onset of various inflammatory diseases, metabolic diseases, autoimmune diseases and/or fibrotic diseases in the prior art. Thus, the peptide can be used for the treatment of inflammatory diseases, metabolic diseases, autoimmune diseases and/or fibrotic diseases by controlling the intracellular concentration of ATF3, and the effect of treating diseases can be increased by further fusing a peptide having intracellular permeability and an inflammation inhibitory function to the peptide.

SEQUENCE FREE TEXT

An electronic file is attached.

The invention claimed is:

1. A peptide represented by any one amino acid sequence selected from the group consisting of SEQ ID NOS: 1 to 4, the peptide having an ability to bind to an ATF3 protein.

2. A fusion peptide comprising the peptide according to claim 1 and a peptide having cell permeability binding to an N-terminus or a C-terminus of the peptide according to claim 1.

3. The fusion peptide according to claim 2, wherein the peptide having cell permeability is represented by an amino acid sequence of SEQ ID NO: 5, SEQ ID NO: 10, or SEQ ID NO: 11.

4. The fusion peptide according to claim 3, wherein the fusion peptide is represented by any one amino acid sequence of SEQ ID NOS: 6 to 9.

5. A method for treating an inflammatory disease comprising administering the peptide according to claim 1 to a subject in need thereof, wherein the inflammatory disease is at least one selected from the group consisting of arthritis, periodontitis, atopy, thyroiditis, uveitis, Hashimoto's thyroiditis, gastritis, steatohepatitis, hepatitis, alcoholic/non-alcoholic steatohepatitis and enteritis.

6. A method for treating a metabolic disease comprising administering the peptide according to claim 1 to a subject in need thereof, wherein the metabolic disease is at least one selected from the group consisting of obesity, weight loss, diabetes, atherosclerosis, arteriosclerosis, cardiovascular diseases, neurological diseases, Alzheimer's disease, cognitive impairment, oxidative stress, skin diseases, skin aging, damage caused by UV irradiation, hypertension, hypercholesterolemia, hyperlipidemia, immunodeficiency, and metabolic syndrome.

7. A method for treating an inflammatory disease comprising administering the fusion peptide according to claim 2 to a subject in need thereof, wherein the inflammatory disease is at least one selected from the group consisting of arthritis, periodontitis, atopy, thyroiditis, uveitis, Hashimoto's thyroiditis, gastritis, steatohepatitis, hepatitis, alcoholic/non-alcoholic steatohepatitis and enteritis.

8. A method for treating a metabolic disease comprising administering the fusion peptide according to claim 2 to a subject in need thereof, wherein the metabolic disease is at least one selected from the group consisting of obesity, weight loss, diabetes, atherosclerosis, arteriosclerosis, cardiovascular diseases, neurological diseases, Alzheimer's disease, cognitive impairment, oxidative stress, skin diseases, skin aging, damage caused by UV irradiation, hypertension, hypercholesterolemia, hyperlipidemia, immunodeficiency, and metabolic syndrome.

* * * * *